(12) United States Patent
Shin

(10) Patent No.: US 11,540,782 B2
(45) Date of Patent: Jan. 3, 2023

(54) METHOD, APPARATUS AND COMPUTER PROGRAM FOR MEASURING AND ANALYSIS OF BLOOD PRESSURE USING PHOTOPLETHYSMOGRAPHY

(71) Applicant: Industry-Academic Cooperation Foundation, Chosun University, Gwangju (KR)

(72) Inventor: Young Suk Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 386 days.

(21) Appl. No.: 16/885,665

(22) Filed: May 28, 2020

(65) Prior Publication Data
US 2020/0375550 A1 Dec. 3, 2020

(30) Foreign Application Priority Data
May 30, 2019 (KR) ........................ 10-2019-0063611

(51) Int. Cl.
*A61B 5/00* (2006.01)
*A61B 5/02* (2006.01)
*A61B 5/021* (2006.01)
*A61B 5/026* (2006.01)

(52) U.S. Cl.
CPC .......... *A61B 5/742* (2013.01); *A61B 5/02007* (2013.01); *A61B 5/02116* (2013.01); *A61B 5/6826* (2013.01); *A61B 5/0261* (2013.01); *A61B 5/7246* (2013.01)

(58) Field of Classification Search
CPC . A61B 5/742; A61B 5/02007; A61B 5/02116; A61B 5/7235–7267; A61B 5/021; A61B 5/02108; A61B 5/02416; A61B 5/6826; A61B 5/0261; A61B 5/7246; A61B 5/7275; A61B 5/0059; A61B 5/743
See application file for complete search history.

(56) References Cited

U.S. PATENT DOCUMENTS

2021/0267550 A1* 9/2021 Mukkamala ............ G06F 3/044

FOREIGN PATENT DOCUMENTS

KR 10-1764527 B1 8/2017

* cited by examiner

*Primary Examiner* — Scott M. Getzow
(74) *Attorney, Agent, or Firm* — Studebaker & Brackett PC

(57) ABSTRACT

A method for measuring and analyzing blood pressure using PPG includes receiving, by a computer, a PPG signal from a finger of a subject, dividing, by the computer, a normalization pulse wave signal derived from the received PPG signal into one or more predetermined windows, extracting, by the computer, a maximum lower amplitude value from one of the respective divided windows, extracting, by the computer, a target feature pattern from the extracted maximum lower amplitude value, deriving, by the computer, a first target unique vector and a second target unique vector with respect to the target feature pattern, using a linear discriminant analysis (LDA) algorithm to display the first target unique vector and the second target unique vector of the target feature pattern on 2-dimensional (2D) graph, and providing, by the computer, a blood pressure state of the subject, using the 2D graph.

10 Claims, 18 Drawing Sheets
(17 of 18 Drawing Sheet(s) Filed in Color)

METHOD, APPARATUS AND COMPUTER PROGRAM FOR MEASURING AND ANALYSIS OF BLOOD PRESSURE USING PHOTOPLETHYSMOGRAPHY

CROSS-REFERENCE TO RELATED APPLICATIONS

A claim for priority under 35 U.S.C. § 119 is made to Korean Patent Application No. 10-2019-0063611 filed May 30, 2019 in the Korean Intellectual Property Office, the entire contents of which are hereby incorporated by reference.

BACKGROUND

Embodiments of the inventive concept described herein relate to a method, an apparatus, and a computer program for measuring and analyzing blood pressure, using photoplethysmography (PPG).

There is an oscillometric blood pressure measuring method, as a non-invasive method for measuring blood pressure.

The oscillometric method refers to a method of measuring blood pressure by detecting and recording the magnitude of the pressure oscillation in a cuff on an artery vessel in a state where the cuff is worn while air pressure is applied to the cuff and then is slowly released.

The conventional oscillometric blood pressure measuring method has problems that wearing the cuff is required and the method is discontinuous.

In the meantime, there are many methods of measuring blood pressure using PPG, as a method of easily measuring blood pressure without using a cuff.

In general, when the blood pressure is measured by using PPG, a method of estimating blood pressure is used by simply analyzing the speed and shape of a pulse wave.

There is a prior art disclosed as Korean Registered Patent Publication No. 10-1764527, on Aug. 14, 2017 (Patent Document 1).

SUMMARY

To improve the discomfort of wearing a cuff, blood pressure measuring methods using PPG that are commonly used have less accuracy by analyzing only the shape of the pulse wave and do not consider other factors capable of affecting the shape of the pulse wave.

Embodiments of the inventive concept provide a method for measuring and analyzing blood pressure that is capable of being quickly and conveniently measured.

Furthermore, embodiments of the inventive concept provide an accurate blood pressure state of a subject by accurately analyzing PPG.

Moreover, embodiments of the inventive concept provide an accurate blood pressure state of the subject by analyzing factors other than the blood pressure capable of affecting PPG.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a method for measuring and analyzing blood pressure using PPG includes receiving, by a computer, a PPG signal from a finger of a subject, dividing, by the computer, a normalization pulse wave signal derived from the received PPG signal into one or more predetermined windows, extracting, by the computer, a maximum lower amplitude value from one of the respective divided windows, extracting, by the computer, a target feature pattern from the extracted maximum lower amplitude value, deriving, by the computer, a first target unique vector and a second target unique vector with respect to the target feature pattern, using a linear discriminant analysis (LDA) algorithm to display the first target unique vector and the second target unique vector of the target feature pattern on 2-dimensional (2D) graph, and providing, by the computer, a blood pressure state of the subject, using the 2D graph. The windows are divided based on a predetermined window region range.

The receiving of the PPG signal includes receiving, by the computer, the PPG signal from an index finger of a right hand and an index finger of a left hand of the subject. The PPG signal includes a PPG signal of the index finger of the right hand and a PPG signal of the index finger of the left hand.

In the dividing, the normalization pulse wave signal is a value of a normalized pulse wave signal by using a value by overall performing square root on a value from adding values obtained by squaring one or more pulse wave signals derived from the PPG signal received by the computer.

The first target unique vector and the second target unique vector are each unique vector value of the subject having a first unique vector in a case of the first target unique vector and a second unique vector in a case of the second target unique vector as axes. The first unique vector and the second unique vector are derived such that each feature pattern of the maximum lower amplitude value derived depending on each pulse wave signal of a normal group, a high blood pressure risk group, and a high blood pressure group is classified into the normal group, the high blood pressure risk group, and the high blood pressure group by using the LDA algorithm. The first unique vector is a first unique vector that occupies a largest classification weight of the feature pattern. The second unique vector is a second unique vector that occupies a second largest classification weight of the feature pattern. The display includes displaying the first target unique vector and the second target unique vector of the target feature pattern with the 2D graph, using the first unique vector and the second unique vector, which are derived to be classified into the normal group, the high blood pressure risk group, and the high blood pressure group, as axes.

The providing of the blood pressure state includes providing the blood pressure state as a blood pressure state of any one of a normal group, a high blood pressure risk group, and a high blood pressure group.

The providing of the blood pressure state includes providing an analysis result considering a factor other than the blood pressure with respect to an overlapping section together when two or more of the normal group, the high blood pressure risk group, and the high blood pressure group overlap with one another.

The factor other than the blood pressure includes at least one of age, weight, workout, whether to take blood pressure medication, elasticity of a blood vessel, calciumation of a blood vessel, or decreased elasticity on capillaries.

The providing of the blood pressure state includes providing the analysis result together in consideration of a case where blood pressure of the subject is classified into the high blood pressure risk group even though the blood pressure of the subject should be classified as the high blood pressure group or a case where the blood pressure of the subject is classified into the normal group even though the blood pressure of the subject should be classified as the high blood pressure risk group when elasticity of a blood vessel is high and providing the analysis result together in consideration of a case where the blood pressure of the subject is classified into the high blood pressure group even though the blood pressure of the subject should be classified as the high blood pressure risk group or a case where the blood pressure of the subject is classified into the high blood pressure risk group even though the blood pressure of the subject should be classified as the normal group when the elasticity of the blood vessel is low.

According to an exemplary embodiment, a computer program for measuring and analyzing blood pressure using PPG that is stored in a medium to execute one method of the method in combination with a computer that is hardware.

According to an exemplary embodiment, a computer apparatus for measuring and analyzing blood pressure using PPG receives a PPG measurement signal from a finger of a subject, divides a normalization pulse wave signal derived from the received PPG measurement signal into one or more predetermined windows, extracts a maximum lower amplitude value from one of the respective divided windows, extracts a target feature pattern from the extracted maximum lower amplitude value, derives a first target unique vector and a second target unique vector with respect to the target feature pattern, using a LDA algorithm to display the first target unique vector and the second target unique vector of the target feature pattern on a 2D graph, and provides a blood pressure state, using the 2D graph. The windows are divided based on a predetermined window region range.

Other details according to an embodiment of the inventive concept are included in the detailed description and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

The above and other objects and features will become apparent from the following description with reference to the following figures, wherein like reference numerals refer to like parts throughout the various figures unless otherwise specified, and wherein.

DETAILED DESCRIPTION

Figure 1:
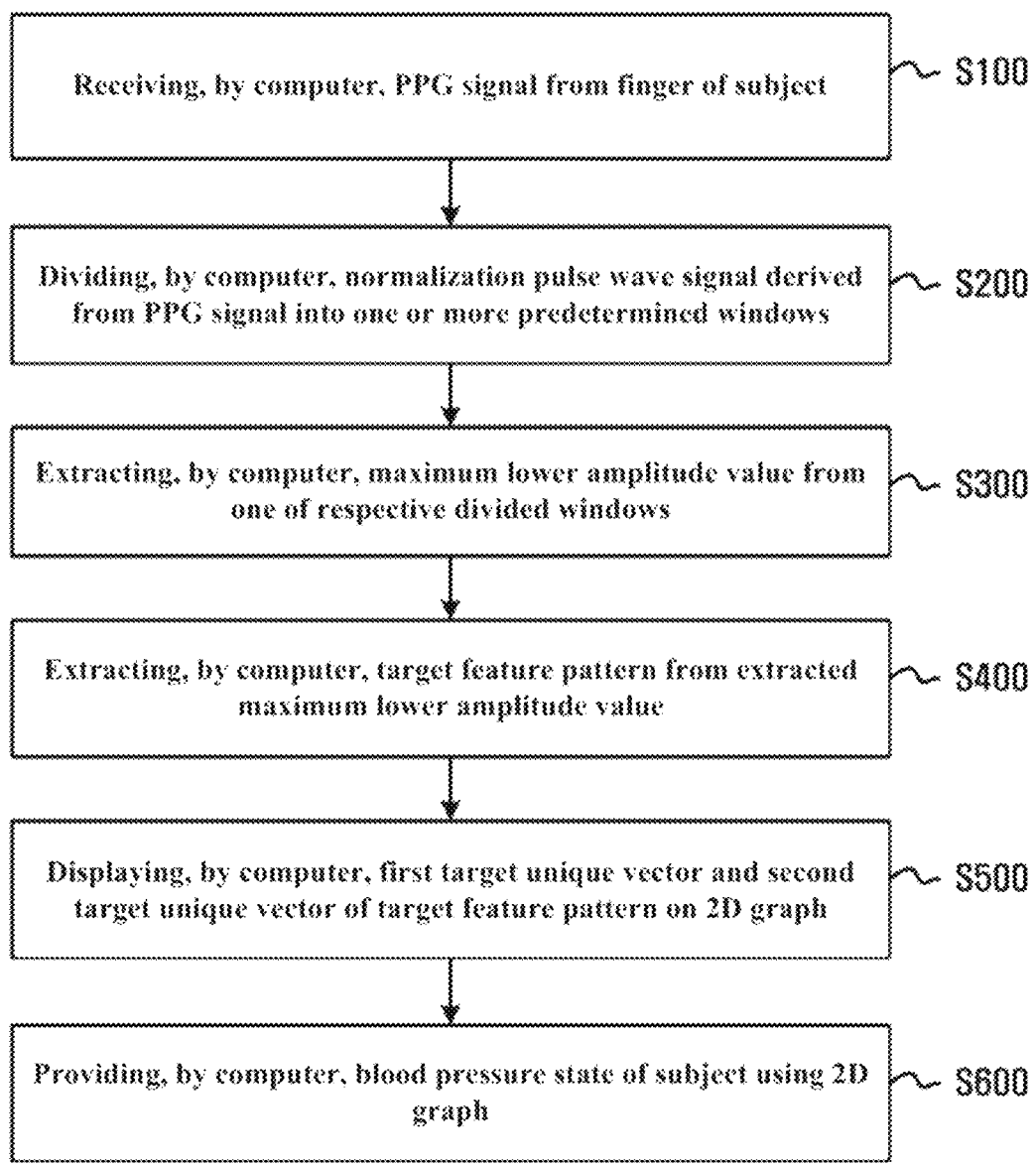
FIG. 1 is a view for describing a method for measuring and analyzing blood pressure using PPG, according to an embodiment of the inventive concept.

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, embodiments of the inventive concept will be described in detail with reference to accompanying drawings.

FIG. 1 is a view for describing a method for measuring and analyzing blood pressure using PPG, according to an embodiment of the inventive concept.

Figure 2:
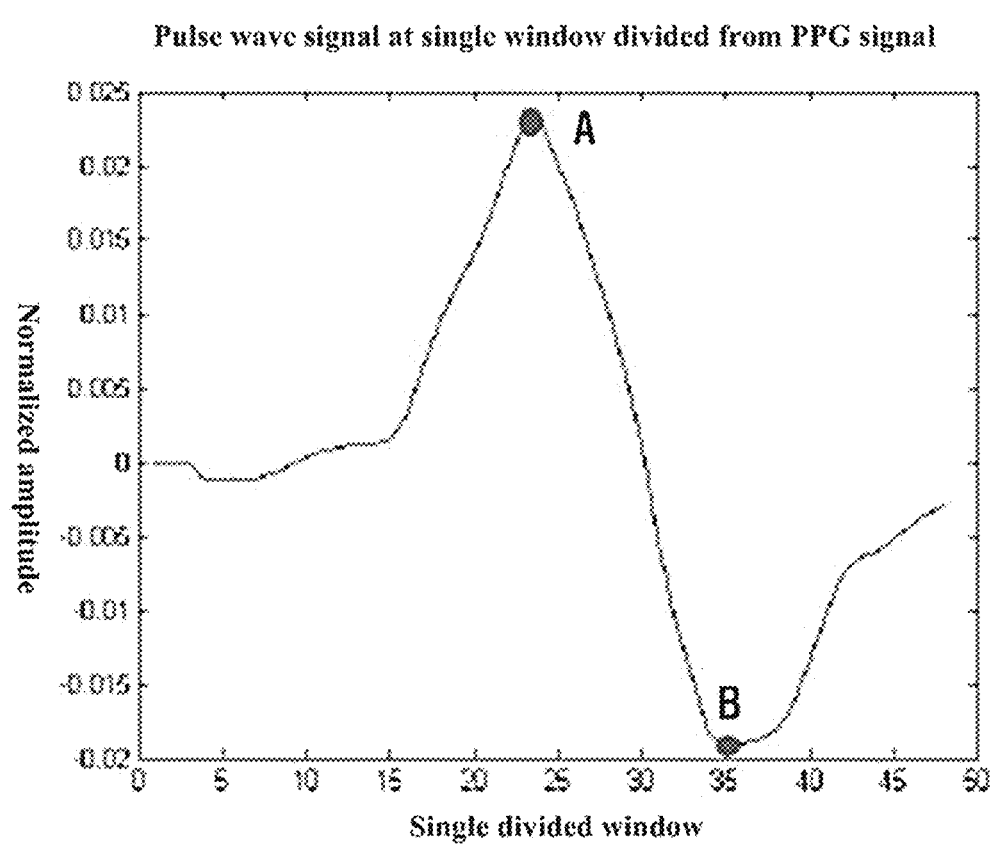
FIG. 2 is a view illustrating the normalized pulse wave signal on the single divided window of the inventive concept.

FIG. 2 is a view illustrating the normalized pulse wave signal on the single divided window of the inventive concept.

Referring to FIG. 1, receiving (S100), by a computer, a photoplethysmography (PPG) signal from the finger of a subject, dividing (S200), by the computer, the normalization pulse wave signal derived from the PPG signal into one or more predetermined windows, extracting (S300), by the computer, the maximum lower amplitude value from one of the respective divided windows, extracting (S400), by the computer, the target feature pattern from the extracted maximum lower amplitude value, displaying (S500), by the computer, the first target unique vector and the second target unique vector from a target feature pattern on a 2-dimensional (2D) graph, and providing (S600), by the computer, the blood pressure state of the subject using the 2D graph are included.

In the receiving (S100), by a computer, of the PPG signal from the finger of the subject, the PPG is a pulse wave measuring method that estimates the heart rate activity state of the subject by measuring the amount of blood flowing into a blood vessel using optical features of biological tissue.

At this time, the method of obtaining a pulse wave through the PPG signal is to extract the pulse waves of capillaries using an infrared sensor and a light receiving sensor.

In the receiving (S100) of the PPG signal from the finger of the subject, the finger of the subject may be at least one of a thumb, an index finger, a middle finger, a ring finger, and a little finger of each of the right and left hands. The receiving (S100) preferably includes receiving the PPG signal from the index fingers of both hands, that is, the index finger of the right hand and the index finger of the left hand.

When the PPG signal is received from the index finger of a right hand and the index finger of a left hand, the PPG signal includes a PPG signal of the index finger of the right hand and a PPG signal of the index finger of the left hand.

The reason that the PPG signal is received from the index fingers of both hands is that the left and right hands have different anatomical structures. Because the left hand is connected to the blood vessel that goes to the heart, there is little effect on lesion; because the right hand is connected to the carotid artery, when an abnormality occurs in the carotid artery, there is an effect on the carotid artery lesion.

Accordingly, the discrimination capacity decreases upon classifying a high blood pressure state with only one hand; when a high blood pressure state is classified by receiving the PPG signal from both hands, a more accurate high blood pressure state may be determined; accordingly, according to the blood pressure measurement method of the inventive concept, the more accurate high blood pressure state may be determined.

The time required to receive the PPG signal may include all the minimum time required to obtain an accurate pulse wave, and is preferably within about 60 seconds to 120 seconds.

In the dividing (S200) of the normalization pulse wave signal into one or more predetermined windows, the computer divides the normalization pulse wave signal derived from the received PPG signal into one or more predetermined windows. The window is divided based on a predetermined window region range.

In particular, a method of deriving the normalization pulse wave signal from the PPG signal first extracts the pulse wave signal of the subject from the PPG signal received by the computer, and samples the pulse wave signal depending on a predetermined sampling condition to generate a desired type of pulse wave signal.

The sampling includes resampling to obtain the predetermined number of data during a predetermined time from the original pulse wave signal of the subject.

The resampling optimizes the original pulse wave signal to generate a smooth pulse wave signal. The optimizing of the pulse wave signal is to perform resampling such that a V-shaped notch is capable of being detected from the pulse wave signal.

The pulse wave signal has a V-shaped notch mainly in one's twenties; as the age decreases, the V-shaped notch on the pulse wave signal appears as a negative value; as the age increases, the V-shaped notch on the pulse wave signal gradually appears as a positive value. When the age is very high, the V-shaped notch may not appear at all on the pulse wave signal.

Accordingly, the age may be predicted based on the form in which the V-shaped notch appears on the pulse wave signal, and thus the original pulse wave signal is optimized and resampled such that the V-shaped notch is capable of being detected from the pulse wave signal.

After the pulse wave signal is optimized such that the V-shaped notch is capable of being detected from the pulse wave signal, the pulse wave signal is resampled based on the specific number of notches.

The above-described resampling and optimization-sampling are equally applied to all original pulse wave signals that are obtained by measuring the same subject multiple times.

Afterward, to reduce the change in pulse wave signals that are changed whenever the same subject is measured, the normalized pulse wave signal is output by normalizing a plurality of pulse wave signals of each optimization-sampled subject.

As described above, the normalization pulse wave signal means that a plurality of pulse wave signals of each subject are normalized.

The pulse wave signal corresponding to the subject is normalized as the normalization pulse wave signal based on Equation 1 below.

Assuming that the total number (e.g., when the number of measurements per person is 5 times and the number of subjects is 10, the number of measurements is 50) of measurements obtained from a subject is W and the number of subjects is N, $W=\{W_1\}_{i=1}^{N}$ may be obtained. Furthermore, the pulse wave signals obtained from the same subject may be expressed as $W_i=\{W_{ij}\}_{j=1}^{N_i}$, and the pulse wave signal $W_{ij}$ means the j-th pulse wave signal of the i-th subject.

$$\varphi=\mathrm{sqrt}(\Sigma_{j=1}^{N_i}(w_{ij})^2)\, W_i^*=W_i/\varphi \qquad \text{[Equation 11]}$$

In Equation 1, the pulse wave magnitude value φ of the same subject is the value obtained by performing square root on the value from adding each of the values obtained by squaring each of the pulse wave signals of the same subject.

Moreover, the normalized pulse wave signal $W_i^*$ is the normalized pulse wave signals obtained by dividing the pulse wave signals of the subject by the magnitude φ of the pulse wave.

It is possible to derive the result of analyzing blood pressure using the accurate analysis of pulse wave signal, by normalizing the pulse wave signal as illustrated in the inventive concept.

Referring to FIG. 2, FIG. 2 illustrates the single divided window, and illustrates a pulse wave signal in the single divided window divided from a PPG signal, as the normalized amplitude.

In FIG. 2, a single pulse is included on the single divided window.

As illustrated in FIG. 2, all of the constant window region ranges on continuous normalization pulse wave signals may be included in the predetermined window region range. However, the single window region includes at least one pulse.

As the single window region includes at least one pulse, the number of windows to be divided and obtained is determined based on the single window region.

In the extracting (S300), by the computer, of the maximum lower amplitude value from one of the respective divided windows, the maximum lower amplitude value is a value corresponding to 'B' in FIG. 2.

In a method of analyzing blood pressure, the blood pressure may be analyzed by selecting specific feature values among various feature values and comparing and classifying the selected feature values on the same line.

At this time, the various feature values are various feature values such as 'A' being the maximum upper amplitude value of FIG. 2, 'B' being the maximum lower amplitude value of FIG. 2, or the average value. One or more feature values may be selected. However, the maximum lower amplitude value is extracted rather than other feature values in the present inventive concept.

When 'A' being the maximum upper amplitude value is a reference, it may be difficult to perform classification due to many overlaps; however, when 'B' being the maximum lower amplitude value is the reference as described in the inventive concept, the number of overlaps is reduced, and thus the classification may be more accurate.

In the extracting (S400), by the computer, of the target feature pattern from the extracted maximum lower amplitude value, the target feature pattern means a unique pattern of the maximum lower amplitude value.

The displaying (S500), by the computer, of the first target unique vector and the second target unique vector from a target feature pattern on the 2D graph is that the computer derives the first target unique vector and the second target unique vector from the target feature pattern by using Linear Discriminant Analysis (LDA) algorithm and displays the first target unique vector and the second target unique vector of the target feature pattern on the 2D graph.

The LDA algorithm is a model for classifying data by learning data distribution and generating a decision boundary.

In general, the LDA algorithm aims to find a straight line capable of best distinguishing categories after the data is projected on a specific axis.

Because the inventive concept also includes the case where data is divided into three categories, it is possible to search for two straight lines on two dimensions as well as a single straight line; when the categories are further subdivided, it is possible to sequentially search for a plurality of straight lines starting from the straight line capable of best distinguishing the categories.

The categories in the inventive concept, which indicate blood pressure states, may be divided into a normal group, a high blood pressure risk group, and a high blood pressure group, and may also be divided into more subdivided groups.

The first target unique vector is a value of each unique vector of the subject having the first unique vector as an axis; the second target unique vector is the value of each unique vector of the subject having the second unique vector as an axis.

At this time, the first unique vector and the second unique vector are derived such that each feature pattern of the maximum lower amplitude value derived depending on each pulse wave signal of a normal group, a high blood pressure risk group, and a high blood pressure group is classified into the normal group, the high blood pressure risk group, and the high blood pressure group by using the LDA algorithm. The first unique vector is the first unique vector that occupies the largest weight of classification of feature patterns. The second unique vector is the second unique vector that occupies the second largest classification weight of the feature patterns.

There are a lot of vectors for explaining the feature pattern in the specific feature pattern. Among the vectors, there are vectors with high explanatory power of the feature pattern, and there are vectors with low explanatory power of the feature pattern.

In the inventive concept, among a lot of vectors indicating feature patterns, the first highly-explanatory vector is derived as the first unique vector being a reference unique vector, and the second highly-explanatory vector is derived as the second unique vector being a reference unique vector.

Furthermore, the first unique vector and second unique vector are vectors that largely occupy a weight for classifying the blood pressure into a normal group, a high blood pressure risk group, and a high blood pressure group, and are vectors that function as an axis for classifying the blood pressure by displaying the target feature pattern on the 2D graph.

Accordingly, the displaying (S500), by the computer, of the first target unique vector and the second target unique vector of the target feature pattern on the 2D graph is to show the first target unique vector and the second target unique vector of the target feature pattern on the 2D graph, using the first unique vector and the second unique vector derived to be classified into a normal group, a high blood pressure risk group, and a high blood pressure group as axes.

The providing (S600), by the computer, of the blood pressure state of the subject using the 2D graph includes providing the blood pressure state of the subject as the blood pressure state of one among a normal group, a high blood pressure risk group, and a high blood pressure group.

When including the providing of the blood pressure state of the subject as the blood pressure state of one among a normal group, a high blood pressure risk group, and a high blood pressure group, the providing (S600) of the blood pressure state of the subject includes providing an analysis result considering factors other than the blood pressure for the overlapping section, in the case where two or more of the normal group, the high blood pressure risk group, and the high blood pressure group overlap with one another.

For example, when the blood pressure state of a specific patient overlaps with the normal group and the high blood pressure risk group or the blood pressure state of a specific patient overlaps with the high blood pressure risk group and the high blood pressure group, the analysis results considering factors other than blood pressure may be provided together with respect to the overlapping section.

The factors other than the blood pressure include at least one of age, weight, workout, whether to take blood pressure medication, the elasticity of a blood vessel, the calciumation of a blood vessel, and the decreased elasticity on capillaries.

Moreover, when the elasticity of the blood vessel is considered as a factor other than blood pressure, in an embodiment, when the elasticity of a blood vessel is high, the providing (S600) of the blood pressure state includes providing the analysis results together in the case where the blood pressure of the subject is classified into the high blood pressure risk group even though the blood pressure of the subject should be classified as the high blood pressure group, or in the case where the blood pressure of the subject is classified into the normal group even though the blood pressure of the subject should be classified as the high blood pressure risk group.

In another embodiment, when the elasticity of a blood vessel is low, the providing (S600) of the blood pressure state includes providing the analysis results together in the case where the blood pressure of the subject is classified into the high blood pressure group even though the blood pressure of the subject should be classified as the high blood pressure risk group, or in the case where the blood pressure of the subject is classified into the high blood pressure risk group even though the blood pressure of the subject should be classified as the normal group.

At this time, the providing (S600) of the blood pressure state may include not only the elasticity of a blood vessel, but also the age of a patient capable of predicting the elasticity of the blood vessel.

In particular, a plurality of target feature patterns are illustrated on the 2D graph of the inventive concept, and the result of analyzing the blood pressure state will be described with reference to FIGS. 3 to 10.

Figure 3:
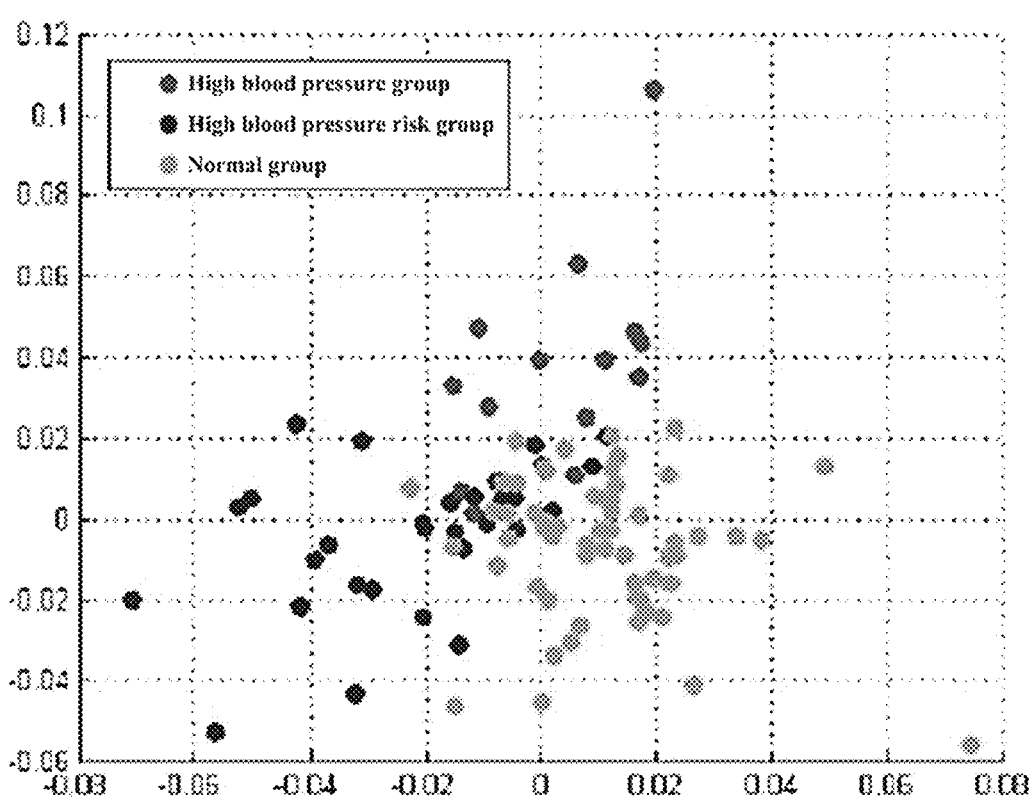
FIG. 3 is a diagram illustrating a pattern of each group of the inventive concept on a single 2D graph.

FIG. 3 is a diagram illustrating a pattern of each group of the inventive concept on a single 2D graph.

Figure 4:
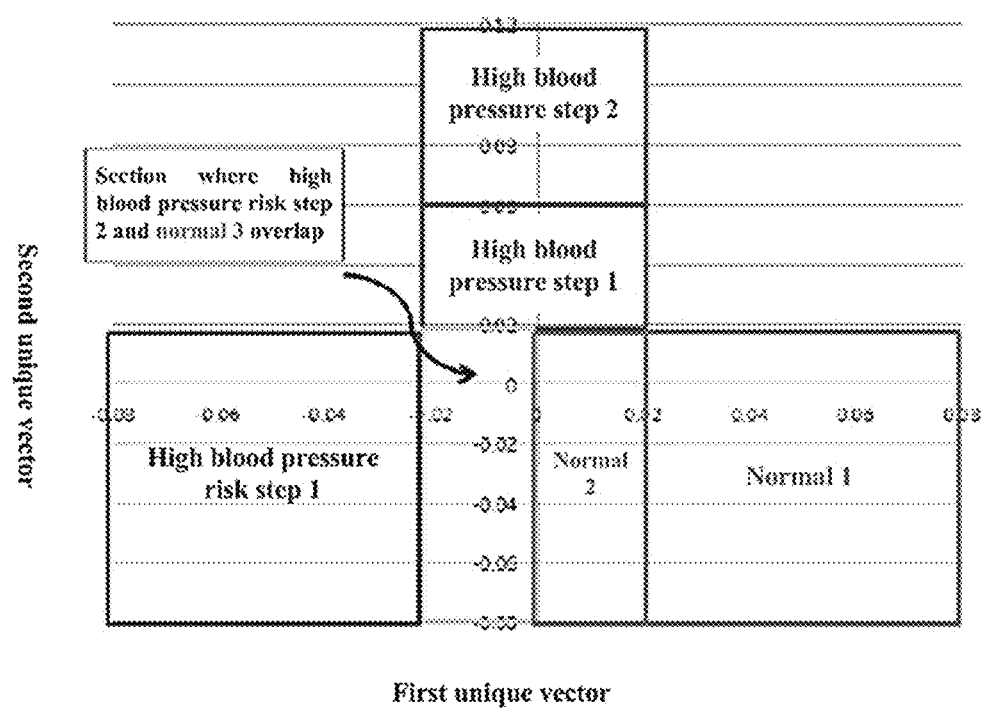
FIG. 4 is a diagram for determining a blood pressure region by using a PPG signal.

FIG. 4 is a diagram for determining a blood pressure region by using a PPG signal.

Figure 5A:
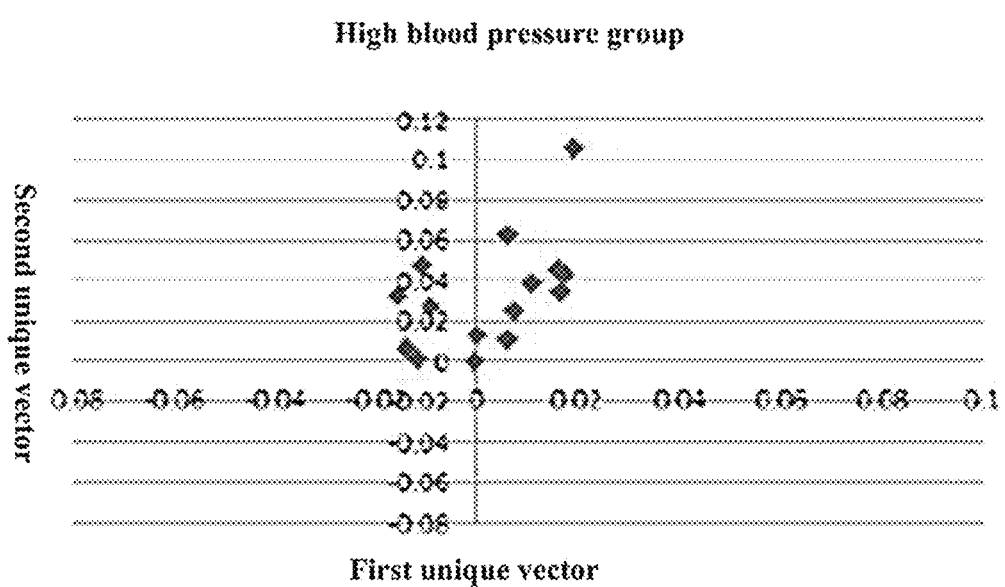
FIGS. 5A to 5C are diagrams illustrating a pattern analysis result of each group for a 2D graph of the inventive concept.
Figure 5B:
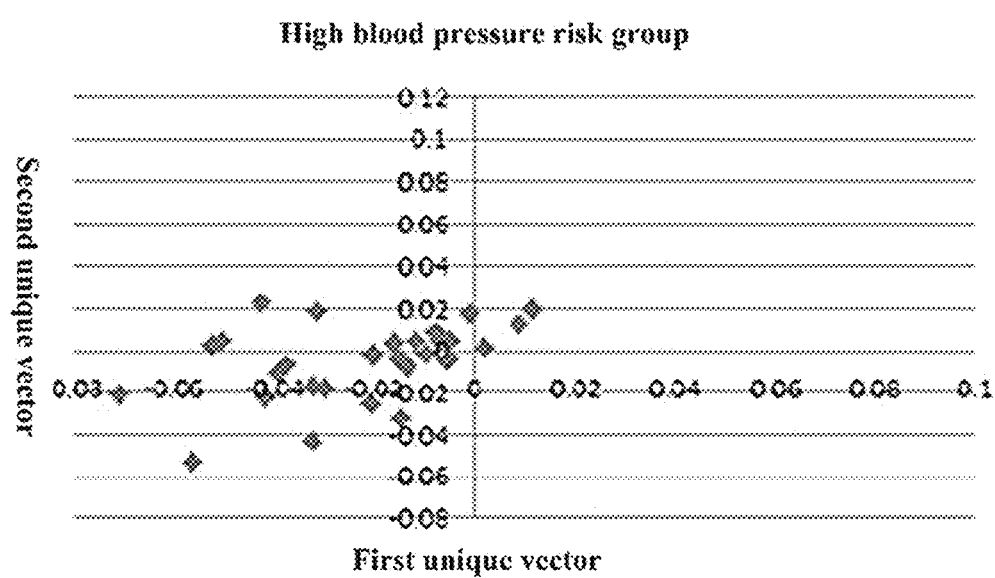
Figure 5C:
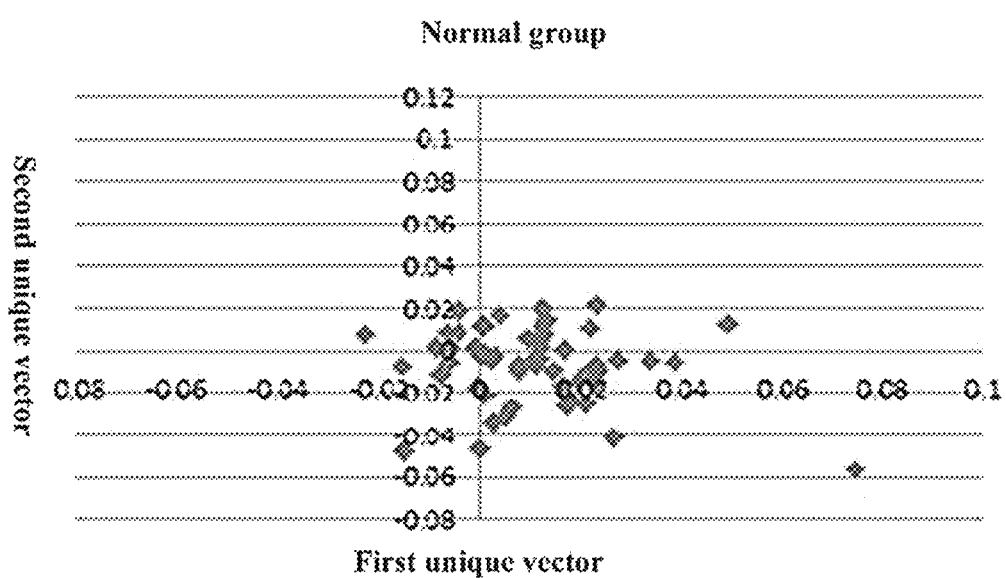

FIGS. 5A to 5C are diagrams illustrating a pattern analysis result of each group for a 2D graph of the inventive concept.

FIGS. 6A to 6C and 7 are diagrams illustrating a pattern analysis result for a high blood pressure group of the inventive concept.

Figure 8A:
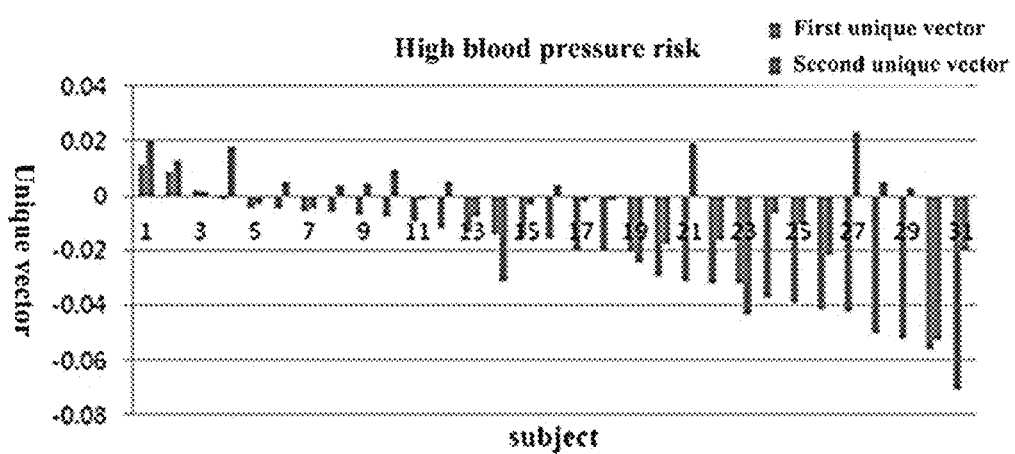
FIGS. 8A to 8C are diagrams illustrating a pattern analysis result for a high blood pressure risk group of the inventive concept.
Figure 8B:
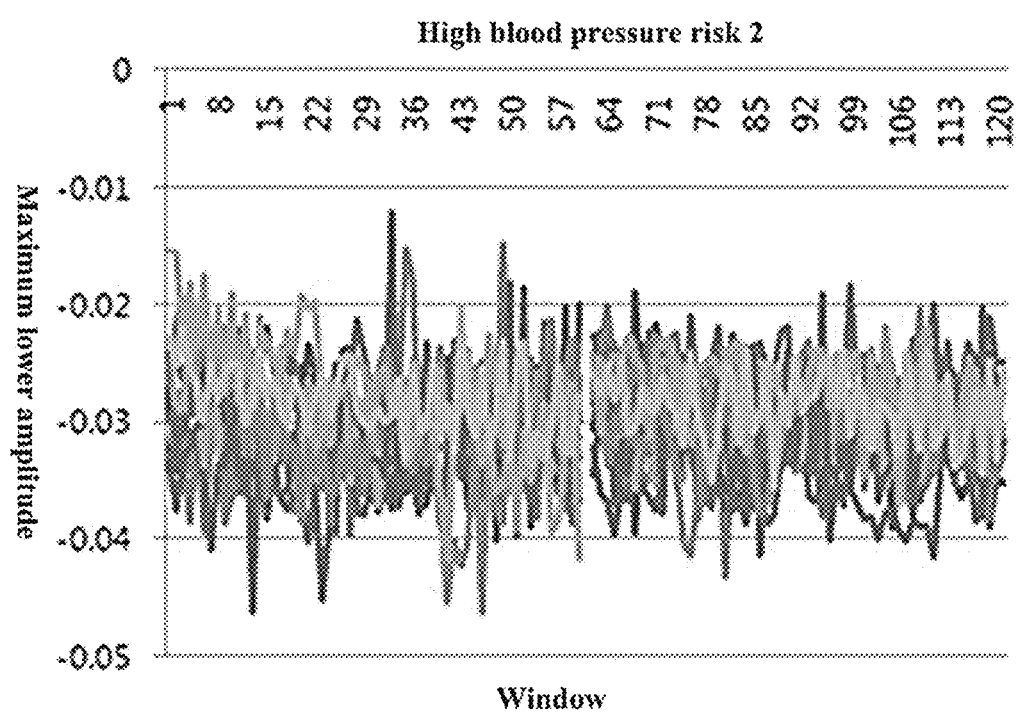
Figure 8C:
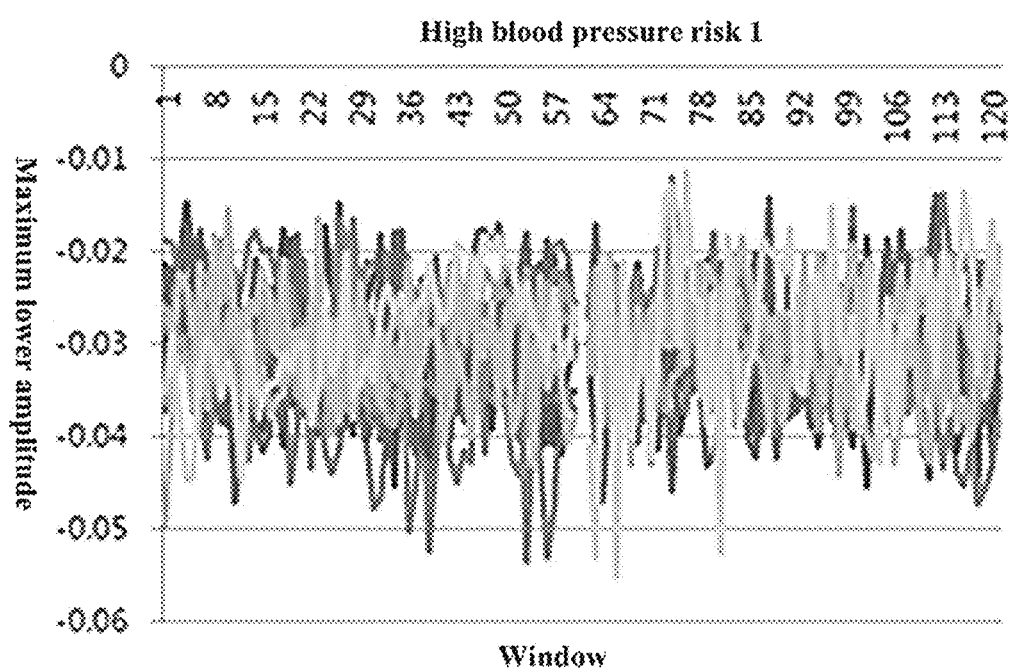
Figure 9:
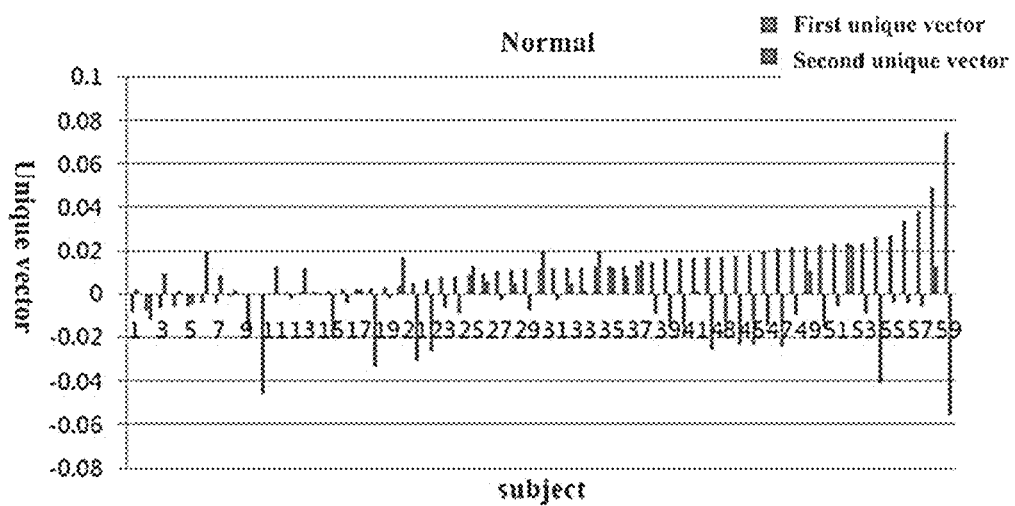
FIGS. 9 and 10A to 10C are diagrams illustrating a pattern analysis result for a normal group of the inventive concept.

FIGS. 8A to 8C are diagrams illustrating a pattern analysis result for a high blood pressure risk group of the inventive concept.

FIGS. 9 and 10A to 10C are diagrams illustrating a pattern analysis result for a normal group of the inventive concept.

FIG. 3 is a graph illustrating all of the patterns of a high blood pressure group, a high blood pressure risk group, and a normal group together on a 2D graph illustrated as a first unique vector and a second unique vector.

Referring to FIG. 3, the high blood pressure group, the high blood pressure risk group, and the normal group are not accurately divided, and overlapping sections are present.

In overlapping sections, there is a need for analysis other than the pattern. Furthermore, in non-overlapping sections, patterns of other groups may appear due to factors other than blood pressure.

Moreover, FIG. 4 illustrates the results classified by using the first unique vector and the second unique vector of LDA in patterns of maximum lower amplitude values derived from the PPG signal on the diagram for determining a blood pressure.

Referring to FIG. 4, in detail, the determination diagram is classified as high blood pressure step 1 (a low blood pressure step in the high blood pressure group), high blood pressure step 2 (a high blood pressure step in the high blood pressure group), high blood pressure risk step 1 (a low blood pressure step in the high blood pressure risk group), high blood pressure risk step 2 (a high blood pressure step in the high blood pressure risk group), normal 1 (a low blood pressure step in the normal group), normal 2 (a normal blood pressure step in the normal group), and normal 3 (a high blood pressure step in the normal group) and is illustrated. The overlapping section is also illustrated on the determination diagram.

Each step will be described in detail based on the classification of FIG. 4.

First of all, referring to FIG. 5, FIG. 5A illustrates the 2D graph of a high blood pressure group; FIG. 5B illustrates the 2D graph of a high blood pressure risk group; FIG. 5C illustrates the 2D graph of a normal group.

Besides, FIGS. 6A to 10C classify blood pressure states in more detail.

Accordingly, each step will be described in detail with reference to FIGS. 5A to 10C.

Referring to FIGS. 5A and 6A to 6C corresponding to the high blood pressure group, in the case of a high blood pressure group, a distribution in which the second unique vector value is not less than '0' appears on the 2D graph expressed with the first unique vector and the second unique vector; the first unique vector is distributed in the range of −0.02 to +0.02; as the positive value of the first unique vector is greater and the positive value of the second unique vector is greater, the blood pressure is higher.

In particular, the second unique vector value in the range of +0.02 to +0.059 indicates the high blood pressure step 1; the second unique vector value in the range of +0.06 or higher indicates the high blood pressure step 2.

Figure 6A:
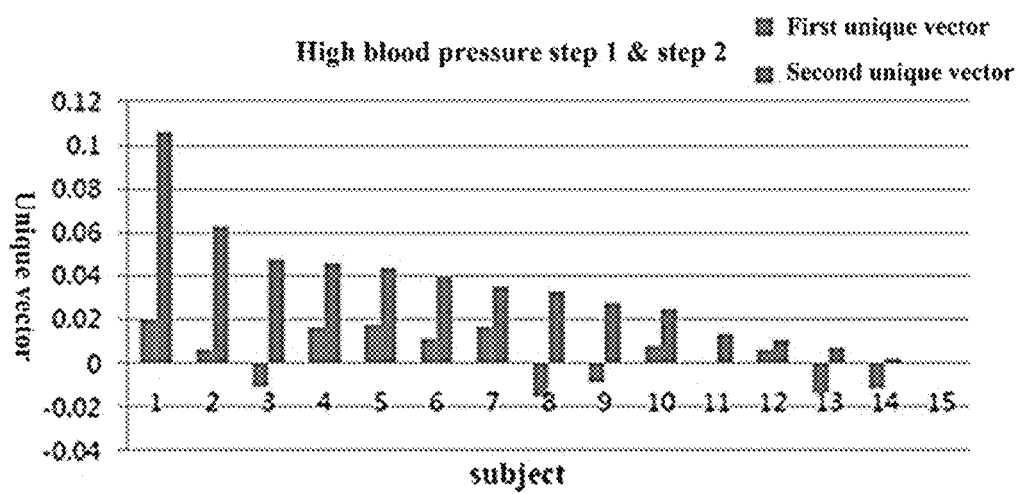
FIGS. 6A to 6C and 7 are diagrams illustrating a pattern analysis result for a high blood pressure group of the inventive concept.
Figure 6B:
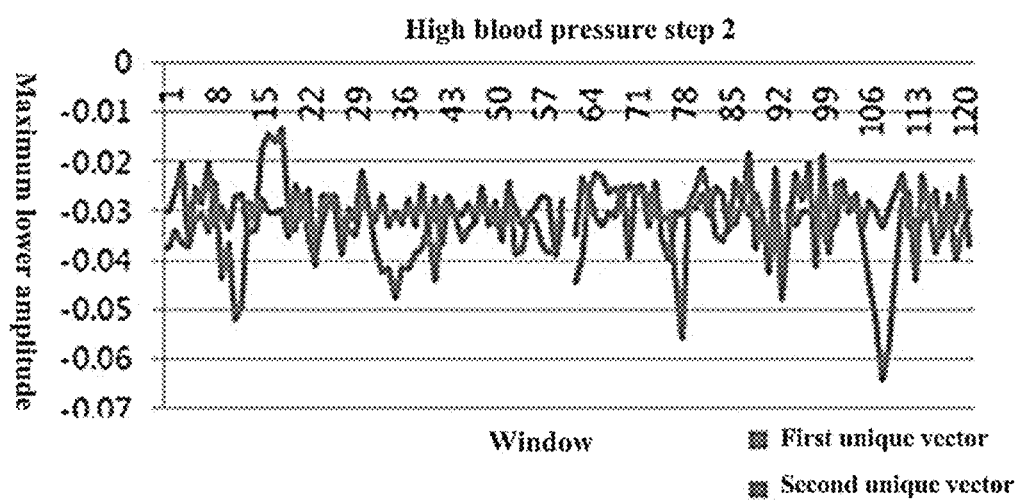
Figure 6C:
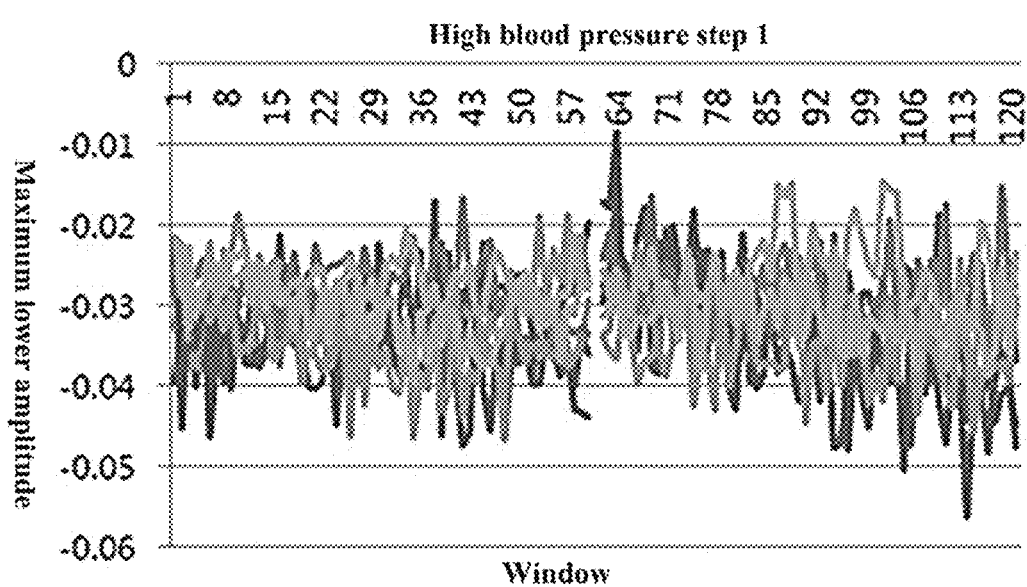

FIG. 6B illustrates the total waveforms of maximum lower amplitudes of the left hand and the right hand of each of the subjects corresponding to a section in which the second unique vector value is not less than +0.06, that is, the high blood pressure step 2; FIG. 6C illustrates the total waveforms of maximum lower amplitudes of the left and right hands of each of subjects corresponding to a section in which the second unique vector value is +0.02 to +0.059.

Referring to FIG. 5A, it may be seen that the pattern rarely occurs in a section in which the value of the first unique vector is between −0.02 and +0.02 and the value of the second unique vector is between 0 and +0.02.

In this case, the corresponding section is a section of the original high blood pressure risk group; when the elasticity of a blood vessel is present even though the corresponding section corresponds to the high blood pressure, the corresponding section indicates the pattern of a high blood pressure risk group, not a pattern of the original high blood pressure group.

Figure 7:
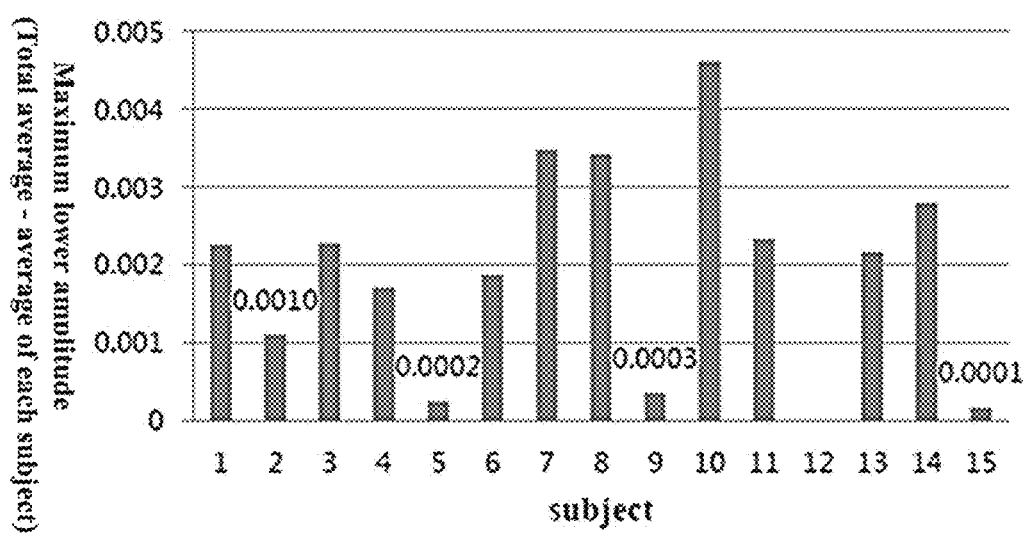

Also, referring to FIG. 7, it is seen that the maximum lower amplitude (the difference between the total average of the high blood pressure group of subjects and the average value of each subject) is less than 0.0010, as subjects having the diastolic BP of a high blood pressure group that is not less than 100. In this case, the flexibility of the elasticity of a blood vessel may decreases and may be reflected to the values of the maximum lower amplitude using PPG.

Referring to FIGS. 5B and 8A to 8C corresponding to the high blood pressure risk group, in the case of the high blood pressure risk group, the main distribution is displayed in the section, in which the value of the first unique vector is negative and the value of the second unique vector is less than +0.02, on the 2D graph expressed with the first unique vector and the second unique vector.

In particular, referring to FIG. 8B, the pattern that appears in the section where the value of the first unique vector is between −0.02 and 0 and the value of the second unique vector is between 0 and +0.02 mostly corresponds to the pattern of middle-aged people (average: 60.5 years), as the high blood pressure risk step 2.

On the other hand, referring to FIG. 8C, the pattern that appears in the section where the value of the first unique vector is less than −0.02 and the value of the second unique vector is not greater than +0.02 mainly corresponds to the pattern of young-aged people (average: 39.2 years old), as the high blood pressure risk step 1.

It may be seen that a pattern rarely appears in a section where the value of the first unique vector is between 0 and +0.02 and the value of the second unique vector is between 0 and +0.02. In this case, as described in FIG. 5A, in the case where there is the elasticity of a blood vessel as the pattern of mainly in the 20s to 30s, a pattern of the normal group, not the pattern of the original high blood pressure risk group appears.

Referring to FIGS. 5C, 9, and 10A to 10C corresponding to the normal group, in the case of the normal group, the main distribution is displayed in the section, in which the value of the first unique vector is not less than −0.02 and the value of the second unique vector is not greater than +0.02, on the 2D graph expressed with the first unique vector and the second unique vector.

Figure 10A:
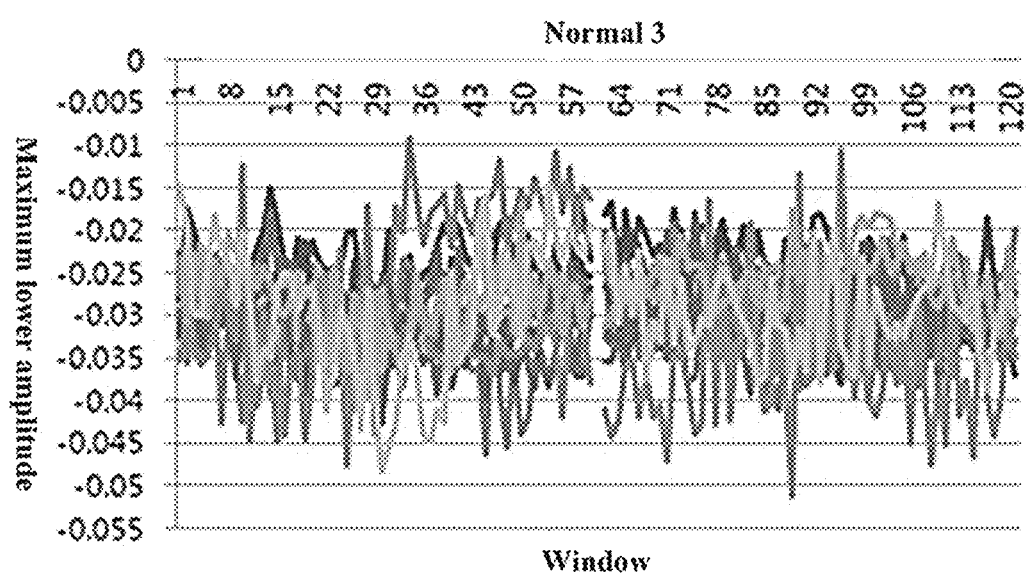

In particular, referring to FIG. 10A, the pattern that appears in the case where the value of the first unique vector is between −0.02 and 0 and the value of the second unique vector is not greater than +0.02 corresponds to the pattern of middle-aged people of 40s or higher, as normal 3. However, the pattern is located in the overlapping section with the pattern distribution of high blood pressure risk step 2.

As described above, the normal blood pressure may have the pattern tendency of partially overlapping with the high blood pressure risk group in the middle-aged people. The reason is that the blood pressure level is normal due to taking blood pressure medication but a normal pattern appears in the high blood pressure risk section due to the aging of blood vessels resulting from aging, the deterioration of elasticity on the capillaries such as the calciumation of blood vessels, or the like.

Figure 10B:
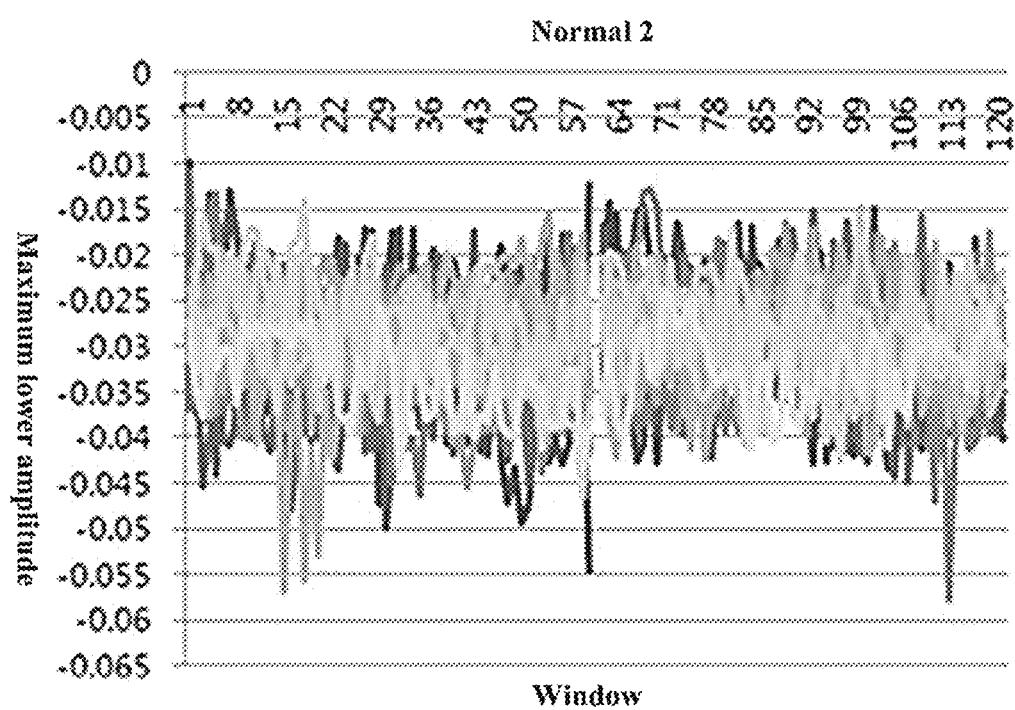
Figure 10C:
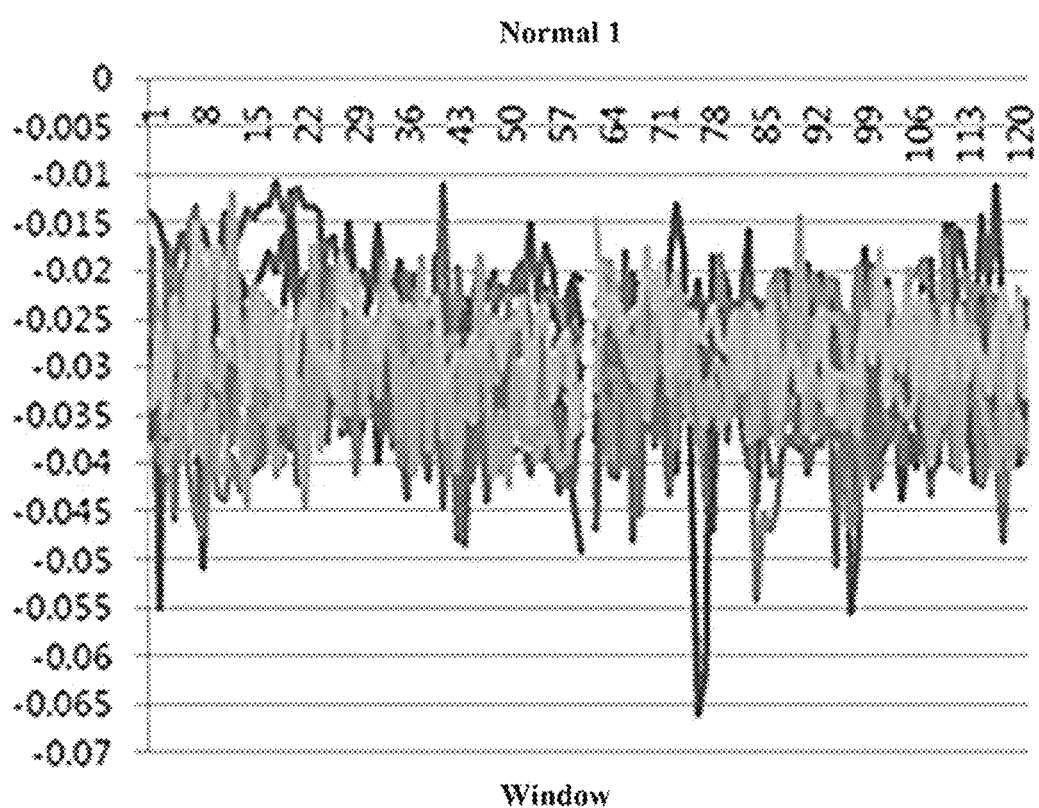

Referring to FIG. 10B, a pattern that appears in the case where the value of the first unique vector is between 0 and +0.02 and the value of the second unique vector is not greater than +0.02 indicates normal 2. Referring to FIG. 10C, a pattern that appears in the case where the value of the first unique vector is greater than +0.02 and the value of the second unique vector is not greater than +0.02 indicates normal 1.

As described above, according to an embodiment of the inventive concept, the blood pressure may be accurately analyzed in consideration of the elasticity of blood vessels and age, instead of classifying the state of blood pressure using only the unique pattern obtained from the PPG of the subject.

Accordingly, to sum up the above-mentioned details, when the blood pressure is simply analyzed based on only the patterns upon analyzing blood pressure, many errors may occur in blood pressure analysis. It is possible to accurately analyze the blood pressure in consideration of age, weight, workout, the elasticity of a blood vessel, whether to take blood pressure medication, the calciumation of a blood vessel, and the decreased elasticity on capillaries, as factors other than the blood pressure.

According to the above-mentioned details, it is possible to further embody the group classification and analysis method of the blood pressure state.

Moreover, according to an embodiment of the inventive concept, the blood pressure state, which is difficult to be accurately analyzed with only the pulse wave derived from the PPG signal, may be analyzed more accurately by applying factors other than the blood pressure, together.

According to another embodiment of the inventive concept, a computer apparatus for measuring and analyzing blood pressure using PPG receives a PPG signal from a finger of a subject, divides the normalization pulse wave signal derived from the received PPG signal into one or more predetermined windows, extracts a maximum lower amplitude value from one of the respective divided windows, extracts a target feature pattern from the extracted maximum lower amplitude value, derives a first target unique vector and a second target unique vector with respect to the target feature pattern, using a LDA algorithm to display the first target unique vector and the second target unique vector of the target feature pattern on 2-dimensional (2D) graph, and provides a blood pressure state of the subject, using the 2D graph. The windows are divided based on a predetermined window region range.

According to an embodiment of the inventive concept, the computer apparatus for measuring and analyzing blood pressure using PPG is applied in the same way as the method for measuring and analyzing blood pressure using PPG described above, in each implementation process and configuration.

The method for measuring and analyzing blood pressure using PPG that is the above-described method according to an embodiment of the inventive concept may be implemented by a program (or an application) for the method for measuring and analyzing blood pressure using PPG and may be stored in a medium such that the program is executed in combination with a computer being hardware.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, blood pressure may be measured quickly and conveniently without a cuff.

Furthermore, according to an embodiment of the inventive concept, it is possible to derive an accurate blood pressure state of a subject, by obtaining PPG and analyzing the feature pattern of a specific amplitude value using a linear discriminant analysis (LDA) algorithm.

Moreover, according to an embodiment of the inventive concept, it is possible to more accurately derive a blood pressure condition, which is difficult to be derived on the graph illustrating the pulse wave, in consideration of the result displayed on the pulse wave and other blood vessel conditions.

Also, according to an embodiment of the inventive concept, even though it is difficult to determine whether the blood pressure belongs to a normal group, a high blood pressure risk group, or a high blood pressure group, it is possible to derive an accurate blood pressure state by considering factors other than blood pressure.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for measuring and analyzing blood pressure using photoplethysmography (PPG), the method comprising:
- receiving, by a computer, a PPG signal from a finger of a subject;
- dividing, by the computer, a normalization pulse wave signal derived from the received PPG signal into one or more predetermined windows, wherein the windows are divided based on a predetermined window region range;
- extracting, by the computer, a maximum lower amplitude value from one of the respective divided windows;
- extracting, by the computer, a target feature pattern from the extracted maximum lower amplitude value;
- deriving, by the computer, a first target unique vector and a second target unique vector with respect to the target feature pattern, using a linear discriminant analysis (LDA) algorithm to display the first target unique vector and the second target unique vector of the target feature pattern on 2-dimensional (2D) graph; and
- providing, by the computer, a blood pressure state of the subject, using the 2D graph.

2. The method of claim 1, wherein the receiving of the PPG signal includes:
- receiving, by the computer, the PPG signal from an index finger of a right hand and an index finger of a left hand of the subject, and
- wherein the PPG signal includes a PPG signal of the index finger of the right hand and a PPG signal of the index finger of the left hand.

3. The method of claim 1, wherein, in the dividing, the normalization pulse wave signal is a normalized pulse wave signal value, which is calculated by using a square root of a total sum of values obtained by squaring one or more pulse wave signals derived from the PPG signal received by the computer.

4. The method of claim 1, wherein the first target unique vector and the second target unique vector are each unique vector value of the subject having a first unique vector in a case of the first target unique vector and a second unique vector in a case of the second target unique vector as axes,
- wherein the first unique vector and the second unique vector are derived such that each feature pattern of the maximum lower amplitude value derived depending on each pulse wave signal of a normal group, a high blood pressure risk group, and a high blood pressure group is classified into the normal group, the high blood pressure risk group, and the high blood pressure group by using the LDA algorithm,
- wherein the first unique vector is a first unique vector that occupies a largest classification weight of the feature pattern,
- wherein the second unique vector is a second unique vector that occupies a second largest classification weight of the feature pattern, and
- wherein the display includes:
- displaying the first target unique vector and the second target unique vector of the target feature pattern with the 2D graph, using the first unique vector and the second unique vector, which are derived to be classified into the normal group, the high blood pressure risk group, and the high blood pressure group, as axes.

5. The method of claim 1, wherein the providing of the blood pressure state includes:
- providing the blood pressure state as a blood pressure state of any one of a normal group, a high blood pressure risk group, and a high blood pressure group.

6. The method of claim 5, wherein the providing of the blood pressure state includes:
- providing an analysis result considering a factor other than the blood pressure with respect to an overlapping section together when two or more of the normal group, the high blood pressure risk group, and the high blood pressure group overlap with one another.

7. The method of claim 6, wherein the factor other than the blood pressure includes at least one of age, weight, workout, whether to take blood pressure medication, elasticity of a blood vessel, calciumation of a blood vessel, or decreased elasticity on capillaries.

8. The method of claim 6, wherein the factor includes elasticity of a blood vessel, and
wherein:
- when the elasticity of the blood vessel is high and blood pressure of the subject is classified into the high blood pressure risk group, providing the analysis result with respect to an overlapping section of the high blood pressure risk group and the high blood pressure group;
- when the elasticity of the blood vessel is high and the blood pressure of the subject is classified into the normal group, providing the analysis result with respect to an overlapping section of the normal group and the high blood pressure risk group;
- when the elasticity of the blood vessel is low and the blood pressure of the subject is classified into the high blood pressure group, providing the analysis result with respect to an overlapping section of the high blood pressure risk group and the high blood pressure group; and
- when the elasticity of the blood vessel is low and the blood pressure of the subject is classified into the high blood pressure risk group, providing the analysis result with respect to an overlapping section of the high blood pressure risk group and the normal group.

9. A non-transitory computer-readable recording medium storing a program for measuring and analyzing blood pressure using PPG, and configured to be coupled to the computer being hardware, the program includes instructions to execute the method of claim 1.

10. A computer apparatus for measuring and analyzing blood pressure using PPG, wherein the computer apparatus:
- receives a PPG measurement signal from a finger of a subject;
- divides a normalization pulse wave signal derived from the received PPG measurement signal into one or more predetermined windows, wherein the windows are divided based on a predetermined window region range;
- extracts a maximum lower amplitude value from one of the respective divided windows;
- extracts a target feature pattern from the extracted maximum lower amplitude value;
- derives a first target unique vector and a second target unique vector with respect to the target feature pattern, using a LDA algorithm to display the first target unique vector and the second target unique vector of the target feature pattern on a 2D graph; and
- provides a blood pressure state, using the 2D graph.

* * * * *